(12) United States Patent
Xu et al.

(10) Patent No.: US 7,148,062 B2
(45) Date of Patent: Dec. 12, 2006

(54) METHOD FOR GENERATING PRIMATE TROPHOBLASTS

(75) Inventors: Ren-He Xu, Madison, WI (US); James A. Thomson, Madison, WI (US)

(73) Assignee: WiCell Research Institute, Inc., Madison, WI (US)

( * ) Notice: Subject to any disclaimer, the term of this patent is extended or adjusted under 35 U.S.C. 154(b) by 442 days.

(21) Appl. No.: 10/389,484

(22) Filed: Mar. 14, 2003

(65) Prior Publication Data

US 2004/0005701 A1 Jan. 8, 2004

Related U.S. Application Data

(60) Provisional application No. 60/365,136, filed on Mar. 15, 2002.

(51) Int. Cl.
*C12N 5/00* (2006.01)
*C12N 5/06* (2006.01)

(52) U.S. Cl. .................... 435/325; 435/363; 435/366

(58) Field of Classification Search ............... 435/325, 435/363, 366
See application file for complete search history.

(56) References Cited

U.S. PATENT DOCUMENTS

| 5,843,780 A | 12/1998 | Thomson |
| 6,200,806 B1 | 3/2001 | Thomson |

FOREIGN PATENT DOCUMENTS

| WO | WO 97/47734 | 12/1997 |
| WO | WO 03/104444 A1 | 12/2003 |

OTHER PUBLICATIONS

Thomson JA, Isolation of a primate embryonic stem cell line, 1995, PNAS, vol. 92, pp. 7844-7848.*
Ross MH, Histology A Text and Atlas 3rd Ed., 1995, pp. 700-706, and 728-731.☐☐.*
The Chimpanzee Sequencing and Analysis Consortium, Initial sequence of the chimpanzee genome and comparison with the human genome, 2005, Nature, vol. 437, pp. 69-87.*
U.S. Appl. No. 10/125,852, filed Feb. 13, 2003, Tang.
U.S. Appl. No. 10/362,533, filed Feb. 5, 2004, Sakano et al.
Janatpour, MJ, et al., "A Repertoire of Differentially Expressed Transcription Factors Taht Offers Insight Into Mechanisms of Human Cytotrophoblast Differentiation," Developmental Genetics (1999) 25:146-157.
Niwa, H, et al., "Quantitative Expression of Oct.-3/4 Defines Differentiation, Dedifferentiation or Self-Renewal of ES Cells," Nature Genetics (2000) 24:372-376.
Schuldiner, M, et al., "Effects of Eight Growth Factors on the Differentiation of Cells Derived From Human Embryonic Stem Cells," PNAS (2000) 97:11307-11312.
Scott, I, et al., "The HAND1 Basic Helix-Loop-Helix Transcription Factor Regulates Trophoblast Differentaition via Multiple Mechanisms," Molecular and Cellular Biology (2000) 20:530-541.
Tanaka, S., et al., "Promotion of Trophoblast Stem Cell Proliferation by FGF4," Science (1998) 282:2072-2075.
Tremblay, GB, et al., "Diethylstilbestrol Regulates Trophoblast Stem Cell Differentiation as a Ligand of Orphan Nuclear Receptor ERRB," Genes & Development (2001) 15:833-838.
Chadwick, K., et al., "Cytokines and BMP-4 promote hematopoietic differentiation of human embryonic stem cells," Blood, 102:906-915 (2003).

* cited by examiner

*Primary Examiner*—Dave Trong Nguyen
*Assistant Examiner*—David A. Montanari
(74) *Attorney, Agent, or Firm*—Quarles & Brady LLP

(57) ABSTRACT

The first method to cause a culture of human and other primate stem cells to directly and uniformly differentiate into a committed cell lineage is disclosed. Treatment of primate stem cells with a single protein trophoblast induction factor causes the cells to transform into human trophoblast cells, the precursor cells of the placenta. Several protein factors including bone morphogenic protein 4 (BMP4), BMP2, BMP7, and growth and differentiation factor 5 can serve as trophoblast-inducing factors.

4 Claims, 1 Drawing Sheet

METHOD FOR GENERATING PRIMATE TROPHOBLASTS

CROSS-REFERENCE TO RELATED APPLICATIONS

This application claims the benefit of U.S. Provisional Application No. 60/365,136 filed Mar. 15, 2002.

STATEMENT REGARDING FEDERALLY SPONSORED RESEARCH OR DEVELOPMENT

Not applicable.

BACKGROUND OF THE INVENTION

Modern cell biology includes a variety of techniques to manipulate various cells of living organisms in vitro. Of particular interest is a category of cell known as a stem cell. Stem cells are undifferentiated or only partially differentiated cells that have the capability to differentiate into a number of progenitor and mature cell lineages and types. The term "stem cells" can be used to refer to a cell type which is the progenitor of a differentiation cellular lineage in a larger organism, such as hematopoietic stem cell, or can refer to totally undifferentiated stem cells which, at least in theory, have the ability to differentiate into any of the tissues of the body. Stem cells are, at a minimum, pluripotent, meaning that they have the potential to differentiate into many different cell types, and may be totipotent, meaning have the potential to differentiate into any cell type of a mature organism of the species. Stem cell cultures have been developed from a variety of tissue types and from a number of different animals.

Recently, it has become possible to generate, culture and maintain cultures of primate embryonic stem cells, including human and rhesus embryonic stem cells. See, for example, U.S. Pat. Nos. 5,843,780 and 6,200,806 to Thomson. Primate embryonic stem cells are stem cultures created from embryos that survive indefinitely in culture and demonstrate the ability to differentiate into the major tissue types of the primate body. Primate embryonic stem cells can be maintained indefinitely in an undifferentiated state in culture, or can be allowed to start a differentiation process by which various of the cells become committed to one or multiple developmental lineages. Typically, the differentiation of stem cells into different tissue types begins with the creation of embryoid bodies, which causes the stem cells in the embryonic body to begin to differentiate into various cell types.

A more differentiated type of human cell of scientific and research interest is a human trophoblast. A trophoblast is a cell which is a precursor of the cells which participate in the formation of the human placenta. When an embryo begins differentiation, at the stage of a blastocyst, the cells in the inner cell mass are committed to form the cells which will become the embryo, while the outer cells of the blastocyst become committed to participate in the development of the placenta. Trophoblast cells have been isolated before, but they are difficult to isolate and have not been available for research in significant amounts. Mouse trophoblast cell lines have been created from blastocyst and post-implantation trophoblasts. Human trophoblast cell lines have been created from transformed placental cells, but techniques to create cultures of primate trophoblasts from embryonic cells or stem cell lines have not yet been reported. While human embryonic stem cells will spontaneously differentiate into a number of differentiated cell types, including some trophoblast cells, this phenomenon has not led to the creation of useful cultures of trophoblast cells. In fact, mouse embryonic stem cells appear to lack the ability to differentiate into trophoblast, and hence, the supply of trophoblasts has always been extremely limited. A replenishable supply of consistent trophoblast cells would be very useful for many pharmaceutical investigations. In particular, the exploration of contraceptive drugs targeting embryo implantation and therapeutics preventing placenta-related birth defects remain the topics of scientific investigation that can be pursued with more ease provided that a source of primate trophoblasts is available.

BRIEF SUMMARY OF THE INVENTION

The present invention is summarized in that a method to induce primate stem cells to predominantly differentiate into human trophoblasts includes the step of culturing the primate stem cells in the presence of a protein trophoblast-inducing factor.

The present invention is also directed to uniform cultures of primate trophoblast cells created by the method taught here.

The present invention is also directed to a method for testing agents on placental cells in which the agents are exposed to trophoblast cultures as described here.

It is an object of the present invention to enable the creation of cultures of nearly pure trophoblasts in a uniform consistent and reproducible manner.

It is a feature of the present invention in that it teaches the first method known to cause primate stem cells in culture to repeatedly, directly, individually and in synchrony predominantly differentiate into a committed cell lineage.

Other objects, features and advantages of the present invention will become apparent from the following specification.

DETAILED DESCRIPTION OF THE INVENTION

Figure 1:
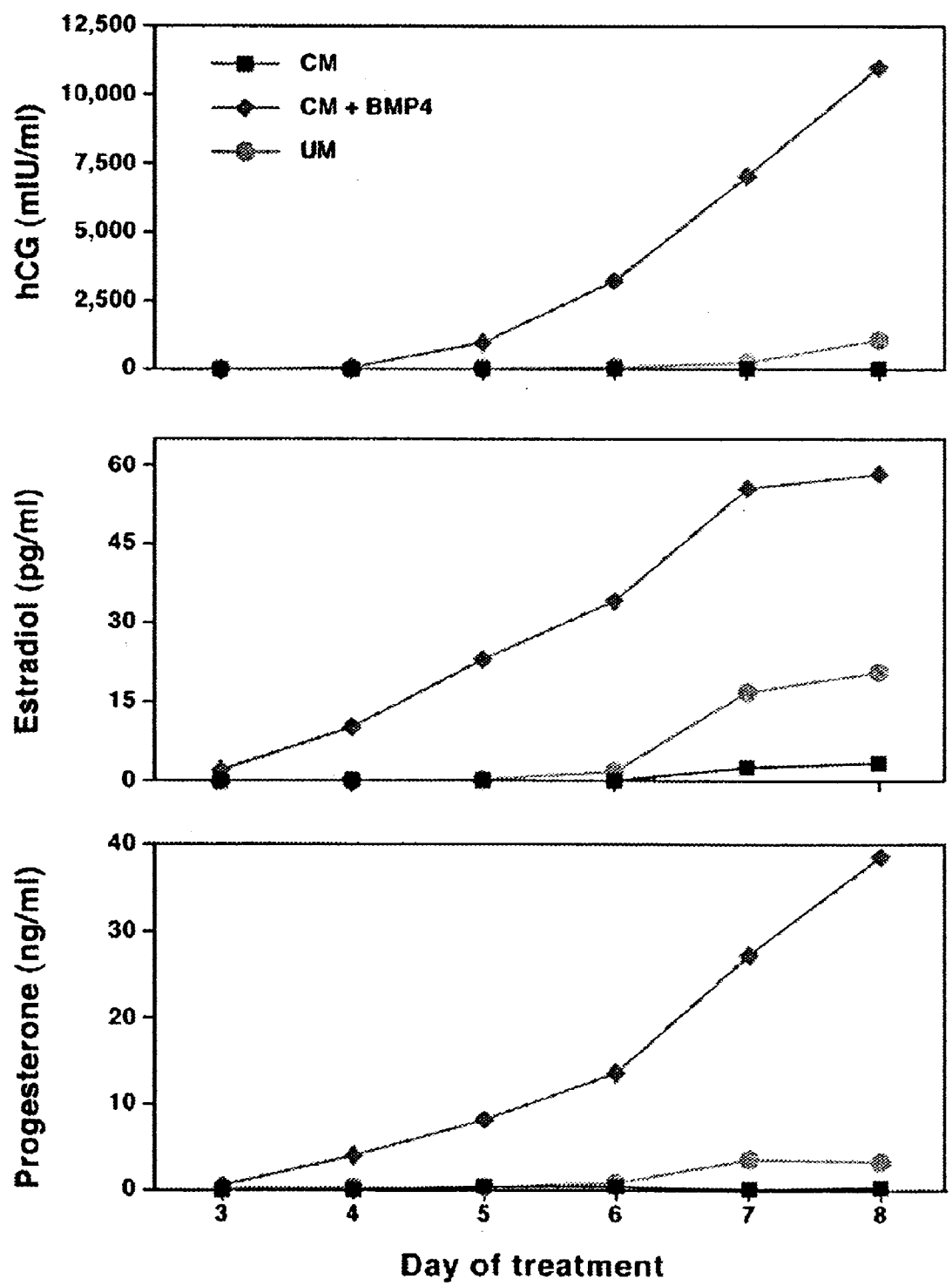
FIG. 1 is a graphical illustration of the secretion of hormones by trophoblast cells cultured according to the present invention.

The present invention is premised on an observation. It has been found by the inventors here that certain protein factors will cause primate embryonic stem cells to differentiate directly into trophoblast cells. The trophoblast cells are stable and exhibit all of the cellular characteristics of placental precursor cells. Since the creation and culture of primate and human embryonic stem cells have become standardized and readily reproducible, this observation makes possible for the first time the creation of a major class of a single cell type (trophoblast cells) directly from a human or other primate stem cell source, Without intervening creation of an embryoid body. It has been found here that the protein factors that cause direct differentiation of primate embryonic stem cells to trophoblast cells include bone morphogenic protein 4 (BMP4) as well as related protein factors such as BMP2, BMP7, and growth and differentiation factor 5 (GDF5). Such a factor is here referred to as a trophoblast-inducing factor.

The availability of human and other primate trophoblast cells in reproducible quantities makes possible many investigative studies on the behavior of placental cells. It is now possible to have a reproducible and inexhaustible supply of placental precursor cells. In particular, it is envisioned that the trophoblast cell cultures can be used for chemical reaction studies to model the behavior of placental cells for use in drug testing, both for general toxicology as well as for specific effects on placental cells. For example, agents, which would inhibit fertilized embryo implantation in a uterus, i.e. birth control agents, can be investigated by observing the effects of putative agents on the trophoblast cell cultures.

This disclosure includes data which demonstrates that human and other primate stem cells can be directly transformed into trophoblast cells by treatment with a single protein factor. As used herein, primate stem cells refers to human or other primate undifferentiated cells which are at least pluripotent. The stem cells used in the examples below originate from human and rhesus embryos, and hence are known as primate embryonic stem cells. Embryonic stem cells are stem cells derived from humans at some stage of development. The method described here is, however, equally applicable to human stem cells derived from other origins, including embryonic germ line cells and stem cells isolated from mature primate bodies. Note that the fact that human stem cells will differentiate into trophoblast cells is unexpected based on experience with mouse stem cells. Efforts to derive trophectoderm tissue from mouse stem cells by manipulation of the external culture environment have so far been unsuccessful, and when formed into chimeras with intact pre-implantation embryos, mouse stem cells rarely contribute to the trophoblast. The failure of mouse embryonic stem cells to form trophoblast cells is consistent with the theory that mouse embryonic stem cells are developmentally similar to primitive ectoderm, which forms after delamination of the primitive endoderm from the inner call mass and which no longer contributes to the trophoblast lineage. The ability of human embryonic stem cells to form trophoblast cells suggests a basic difference between the development potential of mouse and human embryonic stem cells.

Note that the method here involves the application of the trophoblast-inducing factor directly to stem cells in culture, without any intervening processes normally associated with differentiation of stem cells. In particular, note that no stage of transition to embryoid bodies is associated with this method. The differentiation process for stem cells cultured by other means is generally not uniform, in the sense that many different cell lineages or cell types normally result. By contrast, the method described here results in a mass differentiation of the stem cells to a common differentiated cell type, trophoblast.

To demonstrate that the directed differentiation of stem cells into trophoblast cells is due to the influence of the trophoblast-inducing factor, it is possible to inhibit the action of the trophoblast-inducing factor and observed the result. If BMP4 is the trophoblast-inducing factor, this protein can be inhibited by soluble BMP4 receptor or by the antagonizing protein noggin. That is, if one cultures primate stem cells with BMP4 only, the stem cell culture will exhibit large scale directed differentiation to trophoblast cell types. However, if one cultures a similar primate stem cell culture with BMP4 and an inhibitor, such as the soluble BMP4 receptor or noggin, the differentiation to trophoblast cells will not occur.

Human embryonic stem cells in culture have a very distinctive morphology. The cells are small, compact, and uniform, have distinct cell membranes and cluster in groups. The differentiation of stem cells into other cell types is a visible process as the stem cells become larger and more diffuse. Experienced technicians can recognize by cellular appearance of the differentiated cells for many cell types. In the case of trophoblast cells, the cells do become larger and flatten, and the cells membranes becomes diffuse to invisible. However, to supplement the status of the trophoblast cells, various characterizing studies of the cells were undertaken. A gene expression study using DNA microarrays was conducted to examine the gene expression pattern of the cells. The secretion of placental hormones by the cells was also examined. The results were consistent with the identification of these differentiated cells as trophoblast cells. This confirmed that the morphological identification of these cells was correct.

EXAMPLES

A human embryonic stern cells line, H1, was cultured on a Matrigel™—coated plastic plate in medium that had been conditioned on mouse embryonic fibroblasts (MEF) and supplemented with basic fibroblast growth factor (bFGF) at 4 mg/ml. Human bone morphogenic protein 4 (BMP4) (R&D Systems, Minneapolis, Minn., also the source for other recombinant proteins listed here) was applied to the stem cells at concentrations of 1, 10 and 100 ng/ml of culture medium. The stem cells were as a monolayer and not aggregated in embryoid bodies. The H1 cells then underwent a dose and time dependent morphological change, becoming spread out, flat, thin and enlarged or elongated with their nuclei becoming smaller. These changes are consistent with the morphology of trophoblast cells. The morphological changes began with the cells at the edge of each colony and spread inward from there. The changing morphology became evident on day 2 for cultures treated with 100 ng/ml BMP4, day 3 or 4 for cultures treated with 10 ng/ml and days 4 to 5 for cultures treated with 1 ng/ml BMP4.

Similar experiments were conducted with other members of the BMP4 protein signal family. Proteins which have been demonstrate to activate a similar effect, to cause stem cells to change to trophoblast cells, include BMP2, BMP7, and growth and differentiation factor 5 (GDF5). Other proteins, including members of the TGF superfamily, such as TGF beta 1 and activin, were found not to activate this same morphological change in stem cells. Similar morphological changes were observed on rhesus embryonic stem cell lines treated with BMP4, BMP2, BMP7 and GDF5.

The change in morphology of the stem cells treated with the trophoblast-inducing factor is consistent with the morphological changes that occur in the development of an embryo where some cells become committed to a lineage resulting in the placenta. In addition to the morphological changes, the cells begin to express transcription factors GATA2 and GATA3 and chorionic gonadatrophin alpha and beta genes, all of which are expressed in trophoblasts created by other means. The cells produce high amounts of placental hormones including chorionic gonadatrophins, estradiol, and progesterone. The cells continue to secrete these hormones indefinitely. Flow cytometry of the cells demonstrate that the cells are, at least predominantly, CG beta positive.

Experiments were also conducted in which antagonists of BMP family factors were added to the culture at the same time as the protein factor. It was found that if a soluble BMP receptor (at 100 ng/ml) or the BMP antagonizing protein noggin (at 300 ng/ml) were added to the culture at the same time as for BMP4, the morphological change in the stem cells was entirely prevented. This demonstrates the specificity of the effect of the activating protein factor.

Similar experiments were conducted on another stem cell lines, named H9, with similar result in the production of trophoblast cells. In addition, a similar experiment was conducted on H1 cells cultured in the absence of bFGF, suggesting that the effect is universal to human stem cells from various donors and is not dependent on the presence of bFGF.

To further investigate the character of the trophoblasts, cDNA microarrays were used to analyze genes differentially expressed in the BMP4-treated cells and the untreated undifferentiated H1 cells. Of the 43,000 cDNA genes examined on the arrays, a cluster of only 19 clones, representing 14 genes, was strongly upregulated during all the time points examined. Of these 14 genes, 11 have been previously characterized as related to the development of trophoblast or placenta. Many of these genes encode transcription factors, such as transcription factor AP-2 (TFAP2), msh homeobox homolog 2 (MSX2), a suppressor of cytokine signaling 3 (SSI3), GATA binding proteins 2 and 3 (GATA2 and GATA3) and hairy/enhancer-of-spli related with YPRW motif 1 (HEY1). By day 7 of treatment with BMP4, there was also observed a dramatic increase in mRNA expression of many genes known to be expressed in trophoblast or placenta, such as genes encoding CG-$\alpha$ and CG-$\beta$ subunits, luteinizing homone-alpha and placental growth factor. We also sued RT-PCR to observe enhanced expression of trophoblast markers, including CG-$\beta$, glial cells missing-1 (GCM1), the non-classical HLA class I molecule HLA-G1, and CD9. All of the top ten upregulated clones, representing 8 genes, in the microarray analysis, with one exception, encode proteins or peptides previously associated with genes expressed in trophoblast cells. By contrast, after 7 days of BMP4 treatment, transcripts of several genes highly expressed in pluripotent cells had declined, such as those encoding the POU domain, class 5, transcription factor 1 (POU5F1, also known as OCT4), and telomerase reverse transcription factor (TERT).

To further confirm the character of the cells, the amount of the placental hormones CG, estradiol and progesterone secreted into the medium of the cells was examined. H1 cells treated with BMP4 showed markedly higher concentrations of each hormone as compared to undifferentiated cells or cells differentiated in unconditioned medium. FIG. 1 illustrates the time course in the increase of these hormones in the cells exposed to BMP4 (CM+BMP4) as compared to cells without BMP4 (CM) and cells permitted to differentiate in unconditioned medium (UM).

We claim:

1. A method to induce human embryonic stem cells to differentiate into human trophoblast cells comprising the step of culturing the human stem cells in a culture medium comprising presence of a protein trophoblast inducing factor selected from the group consisting of bone morphogenetic protein 4 (BMP4), bone morphogenetic protein 2 (BMP2), bone morphogenetic protein 7 (BMP7), and growth and differentiation factor 5 (GDF5), to cause said stem cells to differentiate into human trophoblast cells.

2. The method of claim 1 wherein the factor concentration is between 1 and 100 nonograms per milliliter of the culture medium.

3. A method to induce primate embryonic stem cells to differentiate into primate trophoblast cells comprising the step of culturing the primate stem cells in a culture medium comprising presence of a protein trophoblast-inducing factor selected from the group consisting of bone morphogenic protein 4 (BMP4), bone morphogenic protein 2 (BMP2), bone morphogenic protein 7 (BMP7) and growth and differentiation factor 5 (GDF5).

4. The method of claim 3 wherein the factor concentration is between 1 and 100 nanograms per milliliter of the culture medium.

* * * * *

UNITED STATES PATENT AND TRADEMARK OFFICE
CERTIFICATE OF CORRECTION

| | | |
|---|---|---|
| PATENT NO. | : 7,148,062 B2 | Page 1 of 1 |
| APPLICATION NO. | : 10/389484 | |
| DATED | : December 12, 2006 | |
| INVENTOR(S) | : Ren-He Xu and James A. Thomson | |

It is certified that error appears in the above-identified patent and that said Letters Patent is hereby corrected as shown below:

Column 6, line 26, please correct the spelling of "nonograms" to --nanograms--.

Signed and Sealed this

Seventh Day of August, 2007

JON W. DUDAS
*Director of the United States Patent and Trademark Office*